Figure 1:
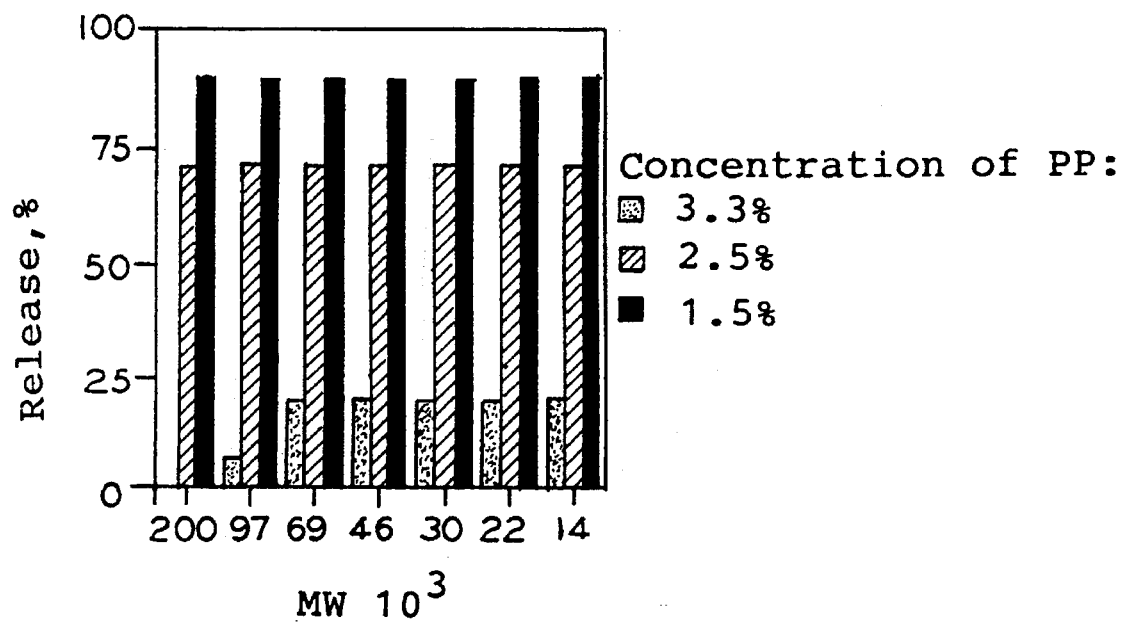

United States Patent [19]

Andrianov et al.

[11] Patent Number: 5,529,777
[45] Date of Patent: Jun. 25, 1996

[54] HYDROGEL MICROENCAPSULATED VACCINES

[75] Inventors: Alexander K. Andrianov, Belmont; Sharon A. Jenkins, Peabody; Lendon G. Payne, Arlington; Bryan E. Roberts, Cambridge, all of Mass.

[73] Assignee: Virus Research Institute, Cambridge, Mass.

[21] Appl. No.: 147,781

[22] Filed: Nov. 4, 1993

Related U.S. Application Data

[63] Continuation-in-part of Ser. No. 90,841, Jul. 12, 1993.

[51] Int. Cl.⁶ .......................... A61K 39/00; A61K 39/38; A61K 9/50; A61K 9/14
[52] U.S. Cl. .................... 424/184.1; 424/189.1; 424/215.1; 424/212.1; 424/219.1; 424/217.1; 424/238.1; 424/210.1; 424/209.1; 424/249.1; 424/468; 424/78.01; 424/489; 424/499
[58] Field of Search ............................ 424/88, 78.08, 424/89, 92, 184.1, 189.1, 215.1, 468, 217.1, 78.01, 212.1, 489, 219.1, 499, 238.1, 209.1, 249.1, 210.1

[56] References Cited

U.S. PATENT DOCUMENTS

| | | | |
|---|---|---|---|
| 4,880,622 | 11/1989 | Allcock et al. | 424/78 |
| 5,075,109 | 12/1991 | Tice et al. | 424/88 |
| 5,149,543 | 9/1992 | Cohen et al. | 424/499 |

FOREIGN PATENT DOCUMENTS

| | | |
|---|---|---|
| 0333523 | 9/1989 | European Pat. Off. . |
| 9004963 | 5/1990 | WIPO .............. A61K 9/50 |

OTHER PUBLICATIONS

Espraza et al. 1992. Parameters affecting the immunogenicity of microencapsulated tetanustoxoid. Vaccine. 10:714–720.

Eldridge et al. 1991. Biodegradable microspheres as a vaccine delivery system. Mol. Immunol. 28(3):287–294.

Eldridge et al. 1990. Controlled vaccine release in the gut–associated lymphoid tissues . . . J. Controlled Release. 11:205–214.

Langer. 1990. New Methods of Drug Delivery. Science 249:1527–1533.

Letvin 1993. Vaccines against human immunodeficiency virus–progress and prospects. NEJ Med. 329(19):1400–1405.

*Primary Examiner*—James C. Housel
*Assistant Examiner*—N. M. Minnifield
*Attorney, Agent, or Firm*—Elliot M. Olstein; Raymond J. Lillie; Gregory D. Ferraro

[57] ABSTRACT

Water soluble polymers or polymeric hydrogels are used to encapsulate antigen to form vaccines. The antigen is mixed with a polymer solution, microparticles are formed of the polymer and antigen, and, optionally, the polymer is crosslinked to form a stable microparticle. Preferred polymers are alginate and polyphosphazenes, and mixtures thereof. Microparticles can be adminstered parenterally or mucosally. For oral delivery, the microparticles are preferably fifteen microns or less in diameter, and adhere to the mucosal lining of the gastrointestinal tract, increasing uptake by the reticuloendothelium.

20 Claims, 6 Drawing Sheets

Water-soluble degradation products in supernatant

HYDROGEL MICROENCAPSULATED VACCINES

BACKGROUND OF THE INVENTION

The present invention is a microsphere configured vaccine vehicle based on a water soluble polymer or hydrogel.

This is a continuation in part of U.S. Ser. No. 08/090,841 entitled "Phosphazene Polyelectrolytes as Immunoadjuvants" filed Jul. 12, 1993.

Induction of an Immune Response via Mucosal Surfaces

The majority of viruses utilize mucosal surfaces as the primary site of infection. Depending on the virus, the infection either remains localized to the mucosal surface or disseminates to establish a systemic infection. Examples of viruses eliciting local infections are influenza, parainfluenza and common cold viruses which propagate in the respiratory mucosa and rotavirus and the Norwalk agent that replicate in the intestinal mucosa. Viruses that induce systemic viral infections that spread from the mucosa are exemplified by measles, mumps, rubella, polio, hepatitis A and B and herpes viruses.

During the last few years a great deal of information has accrued on the induction of mucosal immunity. In the gut, for example, the immune response is localized to the Peyer's patches embedded in the gut mucosa. Lymphoid tissue at these locations is exposed to the lumen of the gut (gut associated lymphoid tissue, GALT), permitting a constant sampling of the luminal contents. Similar lymphoid tissue called the bronchiolar associated lymphoid tissue (BALT) is located in the respiratory mucosa.

Currently, the majority of viral vaccines establish a state of systemic protective immunity following injection of live attenuated or inactivated virus preparations. The success of such vaccines is due to the induction of a cell mediated and/or humoral immune response in the vaccinee. This systemic immunity prevents the onset of disease by reducing viral replication at the mucosa and eliminating the spread of the virus to important target organs.

The use of injectable vaccines has dramatically reduced the incidence of many viral diseases. Nevertheless, their usage is associated with some undesirable effects. Live attenuated virus vaccines can cause systemic complications whereas inactivated vaccines can cause local reactions and even induce an allergic state. Two important consequences of these vaccine side effects are low compliance and litigation. The former leads to reduced immunity and increased rates of natural infection whereas the latter impedes the improvement of current vaccines and development of new vaccines.

An alternative to the use of injectable vaccines is the oral administration of antigen, especially of a live attenuated virus. Such a vaccine induces both a strong mucosal and systemic immunity mimicking the immune response induced by natural infection with the wild type virus. This constellation of immune responses eliminates not only the systemic spread of virus but also viral replication in the mucosa. Thus, the immune response elicited by a replicating oral vaccine is superior to that induced by injectable live or inactivated vaccines. The best example of this type of vaccine is the live attenuated oral polio virus vaccine (OPV). Unfortunately, oral administration of live virus is limited to those viruses which survive passage through the stomach and which do not easily revert to virulence.

The most effective non-replicating antiviral vaccines thus far developed have been inactivated virus particles. The efficacy of peptide and subunit vaccines in animal models has had limited success and currently there are no human vaccines using these kinds of formulations. In the early years of recombinant DNA engineering, many groups fully expected not only the development of protective immunity but also resolution of safety issues by producing non-infectious viral antigens. Unfortunately, it has become increasingly clear that there is no reason to assume that a viral protein produced in a laboratory expression vector, highly purified and injected into a vaccinee will assume a conformation in vivo which even remotely approximates the antigenic state found in natural infection. To date, the only successful recombinant derived vaccine has been the hepatitis B surface (HBS) antigen synthesized in an eucaryotic (yeast) expression system.

There is a growing body of evidence demonstrating that oral presentation of non-replicating antigens in the particulate state induces both a mucosal and systemic immunity that closely mimics the immunity induced by natural infection. This is in contrast to oral immunization with non-replicating soluble antigens which not only fail to induce systemic immunity but very often induce a state of systemic tolerance. Furthermore, the antigen doses required to elicit this immunity are far lower than that required for parenteral immunization with the same antigen. The major advantages inherent in such a vaccine formulation are the ease of administration and complete safety.

Adjuvants

The advent of modern molecular biology has provided a means of producing immunogens with unprecedented ease and precision. It is ironic that these new methodologies generate purified immunogens that do not generally induce a strong immune response in the absence of an effective adjuvant. The development of improved vaccine adjuvants for use in humans has therefore become a priority area of research. Nevertheless, research on adjuvants has lagged seriously behind the work done on immunogens. For decades the only adjuvant widely used in humans has been alum. Saponin and its purified component Quil A, Freund's complete adjuvant and other adjuvants used in research and veterinary applications have toxicities which limit their potential use in human vaccines. New chemically defined preparations such as muramyl dipeptide and monophosphoryl lipid A are being studied.

The traditional view on how adjuvants exert their effect is that adjuvants such as mineral oil emulsions or aluminum hydroxide form an antigen depot at the site of injection that slowly releases antigen. However, excision of the injection site after three days was found to have little effect on immune responses. Recent studies indicate that adjuvants enhance the immune response by stimulating specific and sometimes very narrow arms of the immune response by the release of cytokines, as reviewed by A. C. Allison and N. E. Byars, in: "*Vaccines: New Approaches to Immunological Problems*" R. W. Ellis, ed., p 431 (Butterworth-Heinemann, Oxford 1992). It is desirable to have an adjuvant that would act as a simple depot for the release of antigens over an extended period.

An area of adjuvant research that has developed over the last few years is the utilization of synthetic polymers in the formulation of a vaccine. Examples of synthetic polymers are the non-ionic block co-polymer surfactants as disclosed in Hunter, R. L. Topics in Vaccine Adjuvant Research, D. R. Spriggs and W. C. Koff (eds.) pp. 89–98 (CRC Press, 1991), which have molecular weights below approximately 10,000 and have a simple structure composed of two blocks of hydrophilic polyoxyethylene (POE) which flank a single block of hydrophobic polyoxypropylene (POP). They are considered to be among the least toxic of surfactants and are widely used in foods, drugs and cosmetics. Some of the large hydrophobic co-polymers are effective adjuvants while closely related preparations are not. There is a correlation between the adjuvant activity of these copolymers with differences in the chain links of the POE and POP. Currently, these adjuvants are used in an oil and water emulsion.

A wide range of polyelectrolytes of various molecular weights have also been shown by Petrov, et al. *Sov. Med. Rev.* Section D Immunology, 4:1–113 (1992), to have an adjuvant activity. Macromolecules bearing either positive or negative charges have displayed a similar immunostimulatory activity. The polyelectrolytes form complexes with antigens through electrostatic and hydrophobic bonds. On the other hand, neutral and uncharged polymers had no effect on the immune response.

Controlled Release of Drugs and Antigens

There is currently considerable interest in the development of controlled release vaccines, since the major disadvantage of several currently available vaccines is the need for repeated administrations. Controlled release vaccines could obviate the need for booster immunizations, which would be particularly advantageous in developing countries, where repeated contact between the healthcare worker and the vaccine recipient is often difficult to achieve. There is a growing body of evidence showing that antigen persisting on the external membrane of follicular dendritic cells and lymph node organs is involved in the recruitment of B memory cells to form antibody secreting cells. The continual release of circulating antibodies suggests this recruitment happens continually. As the level of antigen decreases this allows the well established phenomena of affinity maturation of antibody to occur. Acceptance of the antigen persistence concept has an important implication in vaccine development. Ideally, it would be advantageous to be able to formulate vaccines in a way such that antigen is presented to the immune system and, in particular, the follicular dendritic cells, over an extended period of time.

A number of polymers have been used to entrap antigens, as well as other proteins and compounds. An early example of this is the polymerization of influenza antigen within methyl methacrylate spheres having diameters less than one micron (1,000 nanometers) to form so-called nano particles, reported by Kreuter, *J. Microcapsules and Nanoparticles in Medicine and Pharmacology.* M. Donbrow (Ed)., p. 125–148 (CRC Press 1982). The antibody response as well as the protection against infection with influenza virus was significantly better than when antigen was administered in combination with aluminum hydroxide. Experiments with other particles demonstrated that the adjuvant effect of these polymers depends on particle size and hydrophobicity.

Several factors contribute to the selection of a particular polymer for microencapsulation. The reproducibility of polymer synthesis and the microencapsulation process, the cost of the microencapsulation materials and process, the toxicological profile, the release kinetics and the physico-chemical compatibility of the polymer and the antigens are all factors that must be considered.

Biodegradable polymers may be designed around one of many types of labile bonds. Examples are polycarbonates, polyesters, polyurethanes, polyorthoesters and polyamides. One of the advantages of using a synthetic polymer for microencapsulation, rather than a naturally occurring polymer, is that the relative rates of hydrolysis of these bonds under neutral conditions can be influenced by the substituents to the polymer backbone. Substituent modification can also be used to alter the solubility and hydrophilicity/hydrophobicity of the polymer.

A frequent choice of a carrier for pharmaceuticals and more recently for antigens, is poly (D,L-lactide-co-glycolide) (PLGA). Acceptability by the regulatory authorities remains a significant obstacle for any antigen delivery system. PLGA polymers are biodegradable and biocompatible polyesters which have been used as resorbable sutures for many years, as reviewed by Eldridge, J. H., et al. *Current Topics in Microbiology and Immunology.* 1989, 146:59–66. The entrapment of antigens in PLGA microspheres of 1 to 10 microns in diameter has been shown to have an adjuvant effect.

A major disadvantage of the PLGA system is the use of organic solvents and long preparation times for the microencapsulation of the antigens. The process utilizes a phase separation of a water-in-oil emulsion. The compound of interest is prepared as an aqueous solution and the PLGA is dissolved in a suitable organic solvents such as methylene chloride and ethyl acetate. These two immiscible solutions are coemulsified by high-speed stirring. A nonsolvent for the polymer is then added, causing precipitation of the polymer around the aqueous droplets to form embryonic microcapsules. The microcapsules are collected, and stabilized with a polyelectrolyte such as polyvinyl alcohol (PVA), gelatin, alginate, polyvinylpyrrolidone (PVP), or methyl cellulose, and the solvent removed by either drying in vacuo or solvent extraction. While these preparation conditions have been used successfully for microencapsulation of a variety of peptide drugs and hardy immunogens such as staphylococcal enterotoxin B and keyhole limpet cyanin, as demonstrated by J. H. Eldridge, et al., *Infection and Immunity* 9:2978 (1991), the high shear forces, the use of organic solvents and the long preparation times needed for microencapsulation using PLGA could be detrimental to important epitopes on complex labile immunogens such as enveloped viruses.

It is therefore an object of the present invention to provide materials for encapsulation and delivery by parenteral or mucosal administration of vaccines which do not require the use of organic solvents or long preparation times.

It is another object of the present invention to provide a system for delivery of antigen to mucosal surfaces, especially through oral delivery.

It is a further object of the present invention to provide a delivery system for delivery of antigens which elicits a broad spectrum of immunogenic responses.

It is a still further object of the present invention to provide a delivery system for delivery of vaccines which enhances the immunogenicity of the vaccines.

It is yet another object of the present invention to provide a biodegradable delivery system providing controlled release of antigen.

SUMMARY OF THE INVENTION

Water soluble polymers and polymeric hydrogels are used to microencapsulate antigen for delivery to mucosal surfaces and for the controlled release of antigen at the mucosal surface, or for injection (parenteral administration). In the most preferred embodiment, the encapsulated antigen is administered orally or intranasally. The polymer can be any biocompatible, crosslinkable water-soluble polymer or polymeric hydrogel which can be used to form a microparticle having a diameter of two hundred microns or less, under conditions which are gentle and do not denature the antigen to be incorporated therein. Preferred natural water soluble polymers include alginate, gelatin, pectin, and collagen; preferred synthetic water soluble polymers include poly(acrylamide), poly(methacrylamide), poly(vinyl acetate), poly(N-vinyl pyrrolidone), poly(hydroxyethylmethacrylate), poly(ethylene glycol), polyvinylamines, poly(vinylpyridine), phosphazene polyelectrolytes, and poly(vinyl alcohols); preferred polymers forming hydrogels by ionic crosslinking include salts of poly(acrylic acids) or poly(methacrylic acid), sulfonated polystyrene, quaternary salts of either polyamines or poly(vinylpyridine); and mixtures and copolymers of the polymers or monomers thereof. The most preferred polymers are alginate, polyphosphazenes, and mixtures thereof.

To prepare the encapsulated antigen, the antigen is mixed with a polymer solution, microparticles are rapidly formed of the polymer and antigen without the use of significant quantities of organic solvents, and the polymer is crosslinked ionically or covalently to form a stable biodegradable microparticle. The microparticles adhere to mucosal surfaces such as the mucosal lining of the gastrointestinal tract, increasing takeup by the reticuloendothelium of antigen as it is released over time. The polymers are preferably alginate or a polyphosphazene, most preferably crosslinked ionically with a polyion or divalent cation, such as calcium chloride.

Examples demonstrate the enhanced immunogenicity of polymer encapsulated antigen, alone or in combination with a mucosal stimulant such as cholera toxin, as well as how to manipulate the polymers to alter release rates and humoral response, when administered parenterally, orally, or intranasally.

BRIEF DESCRIPTION OF THE DRAWINGS

FIG. 1 is a graph of the permeability of polyphosphazene microspheres, measured as percent release as a function of encapsulated protein molecular weight and polymer concentration. Rainbow protein markers were microencapsulated in three concentrations of poly[di(carboxylatophenoxy)phosphazene-co-di(glycinato)phosphazene] (PP): 3.3% (dotted bars), 2.5% (hatched bars), and 1.5% (dark bars), and incubated in HEPES buffer pH 7.4 at room temperature for 24 hours before the amount of protein in the supernatant was spectrophotometrically measured.

FIG. 2 is a graph of the effect of molecular weight on erosion profiles of polyphosphazene microspheres, measured as percent mass loss over time in days: PC-GIP, 130 KDa (squares); PCPP, 3900 KDa (diamonds); PC-GIP, 170 KDa (circles); and PCPP, 400 KDa (triangles).

FIGS. 3*a* and 3*b* are molecular weight degradation profiles over time in days for PCPP hydrogels with different starting molecular weights of polyphosphazenes: Mw, molecular weight, Mn, number average molecular weight, initial Mw 3,900 KDa (FIG. 3*a*), and Mw 400 KDa (FIG. 3*b*).

FIG. 4 is a molecular weight degradation profile over time in days for PC-GIPP hydrogel for Mw 170 KDa, comparing molecular weight of polymer in the matrix with molecular weight of polymers in solution.

FIG. 5 is a graph of percent release of polystyrene beads from polyphosphazene microspheres coated with poly-L-lysines of different molecular weights: 12,000 mw (squares), 62,500 mw (diamonds), 140,800 mw (circles), and 295,000 mw (triangles). Fluorescent polystyrene (PS) beads measuring 20 nm in diameter were encapsulated in polymer 1 and then coated with poly-L-lysines of different molecular weights. The coated beads were incubated in HEPES buffer pH 7.4 at room temperature. Polystyrene beads released into the supernatant were measured by quantitative fluorimetry and expressed as a percent of the initially encapsulated beads.

FIGS. 6*a*, 6*b*, and 6*c* are graphs of the flu-specific responses in the sera of animals immunized with flu virus in suspension (FIG. 6*a*), encapsulated flu virus in combination with cholera toxin (CT) in alginate microspheres (FIG. 6*b*), and flu virus encapsulated in alginate microspheres (FIG. 6*c*), measured as antibody titer (reading left to right: IgM, dark bars; IgG, hatched bars; IgA, stipled bars) at 7, 14, 21, and 28 days.

FIG. 7 is the flu specific antibody response in the sera following oral administration of influenza encapsulated in alginate in combination with CT, measured at seven, 14, 21, 28, and 35 days post immunization, for IgM, dark bars; IgG, hatched bars; IgA, stipled bars.

FIG. 8 is a graph of the flu-specific antibody response in the fecal samples following administration orally of influenza in alginate microcapsules in combination with CT, following an oral boost, measured at seven, 14, 21, 28 and 35 days after the boost, for IgM, dark bars; IgG, hatched bars; IgA, stipled bars.

DETAILED DESCRIPTION OF THE INVENTION

In general, microspheres for delivery of antigen are formed by covalent or ionic crosslinking of water soluble polymers or polymers that form hydrogels. In the preferred embodiment, the polymers are formed of water soluble polymers such as alginate or polyphosphazenes which are ionically crosslinked with divalent cations such as calcium ions to form a water-insoluble hydrogel encapsulating antigen. Antigen is mixed with the polymer solution prior to crosslinking to insure dispersion of the antigen throughout the microsphere. More stable microspheres can be formed by further crosslinking the microspheres with a polyelectrolyte such as a polyamino acid.

Polymers useful for making Microspheres

The polymer can be almost any biocompatible, crosslinkable water-soluble polymer or polymeric hydrogel which can be used to form a microparticle having a diameter of ten microns or less, under conditions which are gentle and do not denature the antigen to be incorporated therein. As used herein, a hydrogel is defined as any water-swollen polymer. Water-soluble polymers are those that are at least partially soluble (typically to an extent of at least 0.001% by weight) in water, an aqueous buffered salt solution, or aqueous alcohol solution. Preferred natural water soluble polymers include alginate, gelatin, pectin, and collagen; preferred synthetic water soluble polymers include poly(acrylamide), poly(methacrylamide), poly(vinyl acetate), poly(N-vinyl pyrrolidone), poly(hydroxyethylmethacrylate), poly(ethylene glycol), polyvinylamines, poly(vinylpyridine), phosphazene polyelectrolytes, and poly(vinyl alcohols); preferred polymers forming hydrogels by ionic crosslinking include poly(acrylic acids) or poly(methacrylic acid), sulfonated polystyrene, quaternary salts of either polyamines or poly(vinylpyridine); and mixtures and copolymers of the polymers or monomers thereof. The most preferred polymers are alginate, polyphosphazenes, and mixtures thereof.

The polymers can be crosslinked either by ionic crosslinking, covalent crosslinking or physical crosslinking to render the water-soluble polymers water-insoluble. Gelation by ionic crosslinking of an aqueous based polymer solution at room temperature eliminates the long exposure to organic solvents, elevated temperatures and drying required by polymers dissolved in organic solvents. The polymers can be crosslinked in an aqueous solution containing multivalent ions of the opposite charge to those of the charged side groups, such as multivalent cations if the polymer has acidic side groups or multivalent anions if the polymer has basic side groups. Preferably, the polymers are cross-linked by di and trivalent metal ions such as calcium, copper, aluminum, magnesium, strontium, barium, tin, zinc, and iron, or polycations such as poly(amino acid) s, poly(ethyleneimine), poly(vinylamine), poly(vinylpyridine), polysaccharides, and others that can form polyelectrolyte complexes.

Alginates

The best studied ion crosslinkable polymer is the naturally occurring alginate that is prepared from brown algae for use in foodstuffs, for example, Protanal LF 20/60 (Pronova, Inc., Portsmouth, N.H., USA).

The polymer is cross-linked with a multivalent ion, preferably using calcium chloride or other divalent or multivalent cation.

Polyphosphazenes

The elucidation of a class of ion cross-linkable water soluble polyphosphazenes, described by H. R. Allcock and S. Kwon., Macromolecules 22, 75–79 (1989), has made it possible to generate microspheres containing antigens that throughout preparation are exposed only to an aqueous environment.

The term amino acid, as used herein, refers to both natural and synthetic amino acids, and includes, but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term amino acid ester refers to the aliphatic, aryl or heteroaromatic carboxylic acid ester of a natural or synthetic amino acid.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, heptyl, octyl, nonyl, and decyl.

The term (alkyl or dialkyl)amino refers to an amino group that has one or two alkyl substituents, respectively.

The terms alkenyl and alkynyl, as used herein, refers to a $C_2$ to $C_{20}$ straight or branched hydrocarbon with at least one double or triple bond, respectively.

The term aryl, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O)(lower alkyl), —$CO_2H$, —$SO_3H$, —$PO_3H$, —$CO_2$alkyl, amide, amino, alkylamino and dialkylamino, and wherein the aryl group can have up to 3 substituents.

The term aliphatic refers to hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term "pharmaceutically acceptable ion" refers to an organic or inorganic moiety that carries a charge and that can be administered as a counterion in a phosphazene polyelectrolyte.

The term heteroalkyl, as used herein, refers to an alkyl group that includes a heteroatom such as oxygen, sulfur, or nitrogen (with valence completed by hydrogen or oxygen) in the carbon chain or terminating the carbon chain.

The terms poly[(carboxylatophenoxy)(glycinato) phosphazene], poly[di(carboxylatophenoxy)phosphazene-co-di(glycinato)phosphazene-co-(carboxylatophenoxy) (glycinato)phosphazene] and poly[di(carboxylatophenoxy) phosphazene-co-di(glycinato)phosphazene] as used herein refer to the same polymer.

The polyphosphazene preferably contains charged side groups, either in the form of an acid or base that is in equilibrium with its counter ion, or in the form of an ionic salt thereof.

The polymer is preferably biodegradable and exhibits minimal toxicity when administered to animals, including humans.

Selection of Phosphazene Polyelectrolytes

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

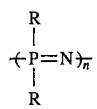

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino- including alkylamino-, heteroalkyl, di(aliphatic)amino- including dialkylamino-, arylamino-, diarylamino-, alkylarylamino-, -oxyaryl including but not limited to -oxyphennyCO$_2$H, -oxyphenylSO$_3$H, -oxyphenylhydroxyl and -oxyphenylPO$_3$H; -oxyaliphatic including -oxyalkyl, -oxy(aliphatic) CO$_2$H, -oxy(aliphatic) SO$_3$H, -oxy(aliphatic) PO$_3$H, and -oxy(aliphatic) hydroxyl, including -oxy(alkyl) hydroxyl; -oxyalkaryl, -oxyaralkyl, -thioaryl, -thioaliphatic including thioalkyl, -thioalkaryl, -thioaralkyl, —NHC(O)O-(aryl or aliphatic), —O—[(CH$_2$)$_x$O]$_y$—CH$_2$)$_x$NH$_2$, —O—[(CH$_2$)$_x$O]$_y$CH$_2$)$_x$NH(CH2)$_x$SO$_3$H, and —O—[(CH$_2$)$_x$O]$_y$—(aryl or aliphatic), wherein x is 1–8 and y is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

In one embodiment, the biodegradable polyphosphazene has the formula:

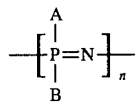

wherein A and B can vary independently in the polymer, and can be:

(i) a group that is susceptible to hydrolysis under the conditions of use, including but not limited to chlorine, amino acid, amino acid ester (bound through the amino group), imidazole, glycerol, or glucosyl; or (ii) a group that is not susceptible to hydrolysis under the conditions of use, including, but not limited to an aliphatic, aryl, aralkyl, alkaryl, carboxylic acid, heteroaromatic, heteroalkyl, (aliphatic)amino- including alkylamino-, heteroaralkyl, di(aliphatic)amino- including dialkylamino-, arylamino-, diarylamino-, alkylarylamino-, -oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H, -oxy(aliphatic)SO$_3$H, -oxy(aliphatic)PO$_3$H, and -oxy-(aliphatic)hydroxyl, including -oxy(alkyl)hydroxyl; -oxyalkaryl, -oxyaralkyl, -thioaryl, -thioaliphatic including -thioalkyl, -thioalkaryl, or thioaralkyl;

wherein the polymer contains at least one percent or more, preferably 10 percent or more, and more preferably 80 to 90 percent or more, but less than 100%, of repeating units that are not susceptible to hydrolysis under the conditions of use, and wherein n is an integer of 4 or more, and preferably between 10 and 20,000.

It should be understood that certain groups, such as heteroaromatic groups other than imidazole, hydrolyze at an extremely slow rate under neutral aqueous conditions, such as that found in the blood, and therefore are typically considered nonhydrolyzable groups for purposes herein. However, under certain conditions, for example, low pH, as found, for example, in the stomach, the rate of hydrolysis of normally nonhydrolyzable groups (such as heteroaromatics other than imidazole) can increase to the point that the biodegradation properties of the polymer can be affected. One of ordinary skill in the art using well known techniques can easily determine whether pendant groups hydrolyze at a significant rate under the conditions of use. One of ordinary skill in the art can also determine the rate of hydrolysis of the polyphosphazenes of diverse structures as described herein, and will be able to select that polyphosphazene that provides the desired biodegradation profile for the targeted use.

The degree of hydrolytic degradability of the polymer will be a function of the percentage of pendant groups susceptible to hydrolysis and the rate of hydrolysis of the hydrolyzable groups. The hydrolyzable groups are replaced by hydroxyl groups in aqueous environments to provide P—OH bonds that impart hydrolytic instability to the polymer.

In other embodiments, the polyphosphazene is: (i) a nonbiodegradable polyphosphazene wherein none, or virtually none, of the pendant groups in the polymer are susceptible to hydrolysis under the conditions of use, or (ii) a completely biodegradable polyphosphazene wherein all of the groups are susceptible to hydrolysis under the conditions of use (for example, poly[di(ethylglycinato)-phosphazene]).

Phosphazene polyelectrolytes are defined herein as polyphosphazenes that contain ionized or ionizable pendant groups that render the polyphosphazene anionic, cationic or amphophilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte contains pendant groups that include carboxylic acid, sulfonic acid, or hydroxyl moieties. While the acidic groups are usually on nonhydrolyzable pendant groups, they can alternatively, or in combination, also be positioned on hydrolyzable groups. An example of a phosphazene polyelectrolyte having carboxylic acid groups as side chains is shown in the following formula:

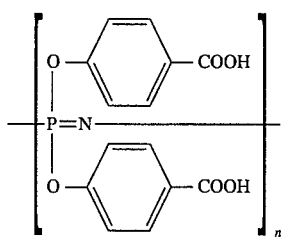

wherein n is an integer, preferably an integer between 10 and 10,000. This polymer has the chemical name poly[di(carboxylatophenoxy)phosphazene]or, alternatively, poly[bis-(carboxylatophenoxy)phosphazene](PCPP).

The phosphazene polyelectrolyte is preferably biodegradable. The term biodegradable, as used herein, means a polymer that degrades within a period that is acceptable in the desired application, typically less than about five years and most preferably less than about one year, once exposed to a physiological solution of pH 6–8 at a temperature of approximately 25° C.–37° C.

Most preferably the polymer is a poly(organophosphazene) that includes pendant groups that include carboxylic acid moieties that do not hydrolyze under the conditions of use and pendant groups that are susceptible to hydrolysis under the conditions of use. Examples of preferred phosphazene polyelectrolytes with hydrolysis-sensitive groups are poly[di(carboxylatophenoxy)phosphazene-co-di(amino acid)phosphazene-co-(carboxylatophenoxy)(amino acid-)phosphazene], specifically including poly[di(carboxylatophenoxy)phosphazene-co-di(glycinato)phosphazene-co-(carboxylatophenoxy)(glycinato)phosphazene], and poly[di(carboxylatophenoxy)phosphazene-co-di(chloro)phosphazene-co(carboxylatophenoxy)(chloro)phosphazene].

The toxicity of the polyphosphazene can be determined using cell culture experiments well known to those skilled in the art. For example, toxicity of poly[di(carboxylatophenoxy)phosphazene] was determined in cell culture by coating cell culture dishes with the poly[di(carboxylatophenoxy-)phosphazene]. Chicken embryo fibroblasts were then seeded onto the coated petri dishes. Three days after seeding the chicken embryo fibroblasts, the cells had become flattened and spindles formed. Under phase contrast microscopy, mitotic figures were observed. These observations provide evidence of the non-toxicity of poly[di(carboxylatophenoxy)-phosphazene] to replicating cells.

Crosslinked polyphosphazenes can be prepared by combining a phosphazene polyelectrolyte with a metal multivalent cation such as zinc, calcium, bismuth, barium, magnesium, aluminum, copper, cobalt, nickel, or cadmium.

Synthesis of Phosphazene Polyelectrolytes

Polyphosphazenes, including phosphazene polyelectrolytes, can be prepared by a macromolecular nucleophilic substitution reaction of poly(dichlorophosphazene) with a wide range of chemical reagents or mixture of reagents in accordance with methods known to those skilled in the art. Preferably, the phosphazene polyelectrolytes are made by reacting the poly(dichlorophosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly-(dichlorophosphazene) and the reaction conditions as necessary.

For example, poly[(carboxylatophenoxy)(glycinato)phosphazene] (PC-GIPP) is prepared by the nucleophilic substitution reaction of the chlorine atoms of the poly-(dichlorophosphazene) with propyl p-hydroxybenzoate and ethyl glycinate hydrochloride (PC-GIPP synthesis). The poly[(aryloxy)(glycinato)phosphazene] ester thus obtained is then hydrolyzed to the corresponding poly(carboxylic acid). Other polyphosphazenes can be prepared as described by Allcock, H. R.; et al., *Inorg. Chem.* 11, 2584 (1972); Allcock, H. R.; et al., *Macromolecules* 16, 715 (1983); Allcock, H. R.; et al., *Macromolecules* 19,1508 (1986); Allcock, H. R.; et al., *Biomaterials* 19, 500 (1988); Allcock, H. R.; et al., Macromolecules 21, 1980 (1988); Allcock, H. R.; et al., *Inorg. Chem.* 21(2), 515–521 (1982); Allcock, H. R.; et al., Macromolecules 22:75–79 (1989); U.S. Pat. Nos. 4,440,921, 4,495,174, 4,880,622 to Allcock, H. R.; et al., U.S. Pat. No. 4,946,938 to Magill, et al., U.S. Pat. No. 5,149,543 to Cohen et al., and the publication of Grolleman, et al., *J. Controlled Release* 3,143 (1986), the teachings of which, and polymers disclosed therein, are incorporated by reference herein.

Selection of an Antigen

The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell-mediated. In the event the material to which the immunogenic response is to be directed is poorly antigenic, it may be conjugated to a carrier such as albumin or to a hapten, using standard covalent binding techniques, for example, with one of the several commercially available reagent kits.

In one embodiment, the polymer is used to deliver nucleic acid which encodes antigen to cells where the nucleic acid is expressed.

Examples of preferred antigens include viral proteins such as influenza proteins, human immunodeficiency virus (HIV) proteins, *Haemophilus influenza,* and hepatitis B proteins, and bacterial proteins and lipopolysaccharides such as gram negative bacterial cell walls and *Neisseria gonorrhea* proteins.

Virus infection of cells in culture generates two kinds of virus particles; mature infectious virus and some non-infectious virus-like particles devoid of nucleic acid. It is preferred to use inactivated mature virus particles in oral vaccines in those cases where the virus replicates to a high titer in cell culture. For virus that either cannot be grown in cell culture or that are tumorigenic, one can use recombinant DNA technology to produce non-replicating virus-like particles (VLPs). Using recombinant technology, one can construct virus-like particles that display on their surface protective antigens (pseudotyping) from virus that because of their inherent complexity do not lend themselves to either of the above two approaches. All of the antigens described above are virus particle structural components, however, not all antigens that elicit protective immunity are structural antigens. In those instances where the protective antigen is a non-structural component, one can genetically fuse such antigens to the surface of self-assembling virus-like particles.

Adjuvants

In some embodiments it may be desirable to include an adjuvant with the antigen which is encapsulated for mucosal or parenteral delivery.

Adjuvants for oral administration

It is known that oral administration of an admixture of trace amounts of cholera toxin (CT) (either cholera toxin subunit A, cholera toxin subunit B, or both) and a second antigen stimulate a mucosal immunity to the coadministered antigen. Furthermore, there is a dramatic humoral immune response to the second antigen instead of the immune tolerance that is elicited by oral delivery of the antigen alone. Thus, mucosally delivered CT functions as a powerful immunostimulant or adjuvant of both mucosal and humoral immunity. The mechanism for this adjuvant effect may be due to the ability of CT to specifically bind to the dome cells (or M cells) overlying the Peyer's patches and then to alter the lymphoid cells in a manner that favors immunoresponsiveness to antigens that may or may not normally bind to the dome cells. Recently, the binding function was localized to the non-toxic B subunit of the cholera toxin (CT-B) molecule. It has now been demonstrated that the addition of CT-B to antigens will mimic the immune response elicited by CT to the same antigens. It is therefore frequently preferred to enhance immunogenicity of the orally administered antigen by including CT in the microencapsulated vaccine.

Adjuvants for parenteral administration

Examples of adjuvants include muramyl dipeptides, muramyl tripeptide, cytokines, diphtheria toxin, and exotoxin A. Commercially available adjuvants include QS-21 from Cambridge Biosciences, Worcester, MA, and monophosphoryl lipid A (MPLA) from Ribi Immunochem.

It is also demonstrated herein that polyphosphazenes can also have an adjuvant effect when administered orally or parenterally. In particular, examples demonstrate the enhanced immunogenicity of microspheres formed of 95% alginate and 5% polyphosphazene (PCPP).

Preparation of an Immunogenic Composition

The polymer is used to encapsulate the antigen, for example, using the method of U.S. Pat. No. 5,149,543 to Cohen, et al., or U.S. Pat. No. 4,352,883 to Lim, et al., the teachings of which are incorporated herein, or by spray drying a solution of polymer and antigen. Alternatively, microspheres containing the antigen and adjuvant can be prepared by simply mixing the components in an aqueous solution, and then coagulating the polymer together with the substance by mechanical forces to form a microparticle.

As used herein, the term "microcapsule" encompasses microparticles, microspheres, and microcapsules unless otherwise stated. In general, those microcapsules which are useful will have a particle diameter of between one and 200 microns, preferably between one and 15 microns for oral administration, and preferably between one and 100 microns for injection, although the limiting factor for injection is the needle size.

In the preferred embodiment, polyphosphazene/antigen solutions are prepared by first dissolving antigen in 1 part 3% $Na_2CO_3$ with stirring, followed by the addition of PCPP with stirring until dissolved and then slowly adding 3 parts phosphate buffer pH 7.4. The detergent Brij58 is added to the stirring polymer solution at a final concentration of 0.2%. The final concentration of PCPP is 2.5%. Sodium alginate/antigen solutions are prepared by dissolving the appropriate amount of antigen in deionized water. The alginate is then slowly added to the antigen solution so that the final concentration of alginate is 1.25%. Constant stirring, as well as the slow addition of the polymer to the antigen, is necessary in order to obtain a homogeneous solution.

In the most preferred embodiment for making microspheres for oral delivery, microspheres are generated using a syringe pump at a speed of 150 µl/min to pump the polymer and antigen solution into an atomization nozzle (Turibotak, Ottawa Canada), or an ultrasonic spray nozzle (Medsonic, Inc., Farmingdale, N.Y.), equipped with an 18 gauge blunt-end needle. The needle enables the solution to be delivered directly to the point of atomization in the nozzle. The polymer solution containing dispersed antigens is then forced through a 1.0 mm orifice in the nozzle under approximately 35 pounds per square inch of air pressure. For polyphosphazenes, the microdroplets cross-link when they impact a 7.5% $CaCl_2$ 0.5% Brij58 bath at a distance 35 cm from the nozzle. The Brij58 is added in order to prevent agglomeration of the microspheres. A 1.5% $CaCl_2$ bath (no Brij58) is used for gelation of alginate microspheres. The microspheres are then quickly transferred to a centrifuge tube and rocked gently for approximately 30 minutes to complete the cross-linking process and to avoid microsphere aggregation as they settle out of the $CaCl_2$ bath. Aggregation may be due to Ca++ crosslinking between exposed carboxylic groups on the microsphere surface and/or hydrophobic interactions between microspheres. After 30 minutes, the microspheres are collected by centrifugation at 4° C., 2800 rpm for 15 minutes. The supernatant is discarded, the pellet is both washed one time and resuspended in sterile deionized water. The microspheres are stored at 4° C. until analysis. Approximately 90% of polyphosphazene microspheres generated under these conditions had diameters in the one to ten micron range.

Larger microspheres are made by using a larger orifice and lower air pressure.

Polymer-Antigen Conjugates

The polymer can also be covalently conjugated with the antigen to create a water-soluble conjugate in accordance with methods well-known to those skilled in the art, usually by covalent linkage between an amino or carboxyl group on the antigen and one of the ionizable side groups on the polymer.

Administration of Immunogenic Composition

Hydrogel microspheres containing antigen can be administered mucosally or parentorally. Nonlimiting examples of routes of delivery to mucosal surfaces are intranasal (or generally, the nasal associated lymphoid tissue), respiratory, vaginal, and rectal. Nonlimiting examples of parentoral delivery include intradermal, subcutaneous, and intramuscular.

Antigens can be encapsulated in both naturally occurring alginate and synthetic polyphosphazenes. The level of antigen loading, release kinetics and the microsphere size distribution are used to vary the resulting immune response. The dosage is determined by the antigen loading and by standard techniques for determining dosage and schedules for administration for each antigen, based on titer of antibody elicited by the polymer-antigen administration, as demonstrated by the following examples.

It will be understood by those skilled in the art that the immunogenic vaccine composition can contain other physiologically acceptable ingredients such as water, saline or a mineral oil such as Drakeol brand mineral oil, Markol brand mineral oil, and squalene, to form an emulsion, or in combination with aqueous buffers, or encapsulated within a capsule or enteric coating to protect the microcapsules from degradation while passing through the stomach.

Storage of Immunogenic Compositions

Ionically cross-linked microspheres need to be stored in buffers that are conducive to the maintenance of their integrity. Conditions have been defined that maintain the integrity of the microspheres as well as antigens entrapped within the polymer matrix. Microspheres containing antigen are stable for seven days stored at 4° C. in sterile deionized water. Standard buffers such as phosphate buffered saline (PBS) cannot be used because the replacement of calcium ions with sodium leads to the liquification of the matrix. Coating the microspheres with an amino acid polymer such as poly L-lysine or other crosslinking agent allows storage in PBS.

The present invention will be further understood by reference to the following non-limiting examples.

EXAMPLE 1

Toxicity Studies

Alginate is approved for human consumption. The polyphosphazenes can be tested to demonstrate non-toxicity using standard methodology. Polyphosphazenes have previously been demonstrated to be non-toxic to living cells. As reported by M. C. Bano, et al., *Bio/Technology*, 9:468 (1991), hybridoma cells were encapsulated in polyphosphazene microspheres having a diameter between 150 and 200 microns. The encapsulated hybridoma cells were able to undergo cell divisions, and by ten days after encapsulation the microspheres were essentially filled with living cells. Additional studies are described herein.

In the first study, cell culture dishes were coated with the polyphosphazene and then chicken embryo fibroblasts seeded onto the coated petri dish. Three days after seeding the chicken embryo fibroblasts, the cells had become flattened and spindle formed and under phase contrast microscopy one could see mitotic figures. This demonstrated the innocuous nature of the polyphosphazenes in cell culture.

In a second in vivo toxicity study, the in vivo acute toxicity of alginate and polyphosphazene was evaluated in 6–8 week old Sprague-Dawley rats. The study consisted of four groups of five male rats/group. Following an overnight fast, each animal in each group received a single oral dose of 5000 mg polymer/kg (in water) via gavage. The dose volume was 20 ml/kg. Group one rats received water and served as a control group. Group two animals received alginate microspheres. Group three rats received alginate microspheres coated with poly-L-lysine (M.W. 68,000). Group four animals received poly[ di(carboxylatophenoxy)phosphazene]microspheres. The animals were clinically observed for 7 days. Body weights were recorded on day 1 prior to immunization and at euthanasia. Blood samples were obtained by puncture of the retro-orbital sinus after anesthetization with $CO_2$ at euthanasia. Animals were food fasted overnight prior to blood collection. Tissues were examined and saved at necropsy.

There were no significant differences in body weight gain between the rats that received microspheres and the rats in the control group. The results of hematology and clinical chemistry were normal for all rats in each group. There were no treatment related abnormalities observed in any organ at necropsy. This study demonstrated that at an oral dose of 5000 mg/kg, polyphosphazene and alginate microspheres are not acutely toxic.

EXAMPLE 2

Incorporation of Proteins and Release Characteristics of microspheres

In order for the microencapsulated antigens to elicit an immune response, the antigen must be released from the microspheres. Antigen is released from a microsphere through the two different but not mutually exclusive processes of diffusion and erosion. If the hydrogel is permeable to the dispersed antigens, then the antigens can simply diffuse out of the microspheres following the water phase that fills the matrix of the microsphere. Release of antigen is, therefore, an indication of the permeability of the microsphere matrix to the antigen. Conversely, adsorption of the antigens to the polymer matrix will serve to either reduce or eliminate the diffusion of the antigen out of the microsphere.

Characterization of release kinetics. Protein molecular weight markers (Amersham) and FITC-labelled bovine serum albumin (Sigma) were microencapsulated to study release kinetics of soluble proteins. The release kinetics of 20 nm polystyrene beads (Duke Scientific) can be used for comparative purposes.

Quantitiation of Protein in Microspheres. For immunogenicity studies, the protein content of microspheres is determined both directly after generation of the microspheres to assess the percent incorporation and also immediately before injection into animals to insure delivery of known antigen quantities.

The protein content of the microspheres can not be assessed by a standard assay such as the Bio-Rad protein assay. Although the protein can be released from the microspheres by chelating the Ca++ responsible for forming the hydrogel, the addition of the Bio-Rad reagent which contains divalent cations causes the polymer to re-cross-link, rendering the antigen unavailable to the dye reagent.

The quantitation of protein antigens encapsulated in ionically cross-linked microspheres is determined by electrophoresing a known quantity of intact microspheres in SDS-PAGE. During electrophoresis, the proteins migrate out of the microsphere matrix and into the polyacrylamide gel. The protein concentration is determined by comparison to known quantities of the encapsulated protein electrophoresed in parallel to the microsphere preparation.

Determination of Microsphere Size. One to fifteen micron microspheres are believed to have an adjuvant effect and are therefore preferred. The size of alginate and polyphosphazene microspheres is measured utilizing a Coulter LS100 Particle sizer. The size is reported as % number in the one to ten micron size range.

Modification of antigen release from polyphosphazene microspheres.

Effect of polymer concentration and molecular weight of the antigen.

The permeability of the poly[di(carboxylatophenoxy) phosphazenes] was investigated by encapsulating protein molecular weight markers (Rainbow protein molecular markers (Amersham Corporation), ranging in molecular weight from 14,000 to 200,000 daltons, that are commonly used in polyacrylamide gel electrophoresis. Release of the proteins was assayed by spectrophotometric measurements of the supernatant.

The results are shown in FIG. 1. The permeability of a particular protein such as the 14.3 KDa molecular weight lysozyme was affected by the concentration of the polymer in the gel. As the polymer concentration rises from 1.5% to 3.3% there is a marked decrease in the diffusion of the protein out of the microcapsule matrix. Similarly, as the molecular weight of the protein increases, diffusion of the protein out of the matrix is retarded. For example, the 200 KDa molecular weight myoglobin protein was unable to diffuse out of a 3.3% polyphosphazene matrix in a time period of 24 hours.

Effect of polymer molecular weight and composition.

Figure 2:
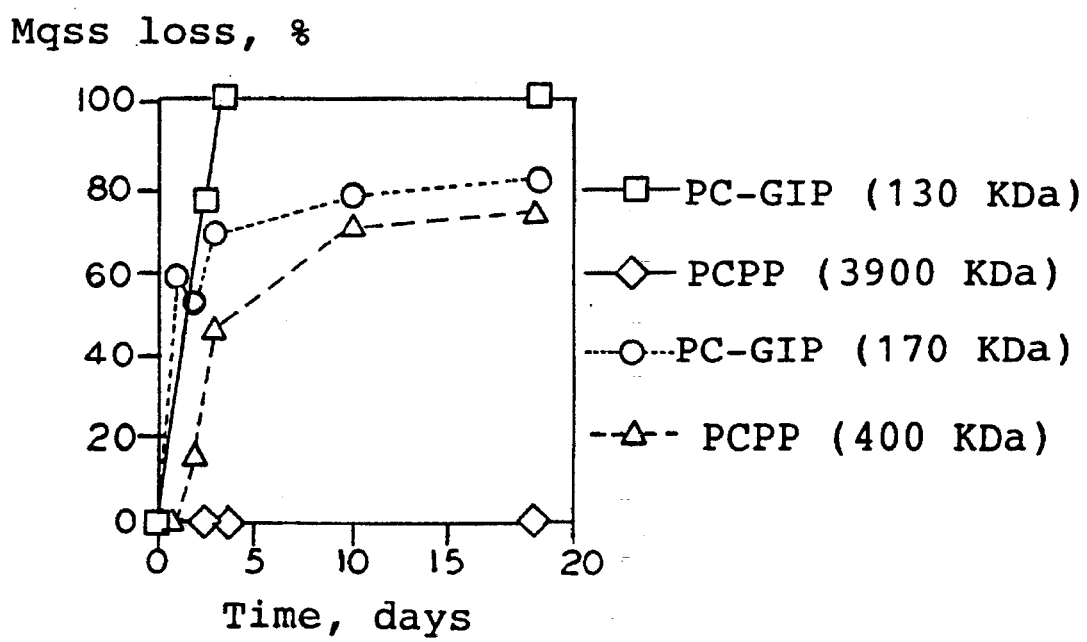
Figure 3A:
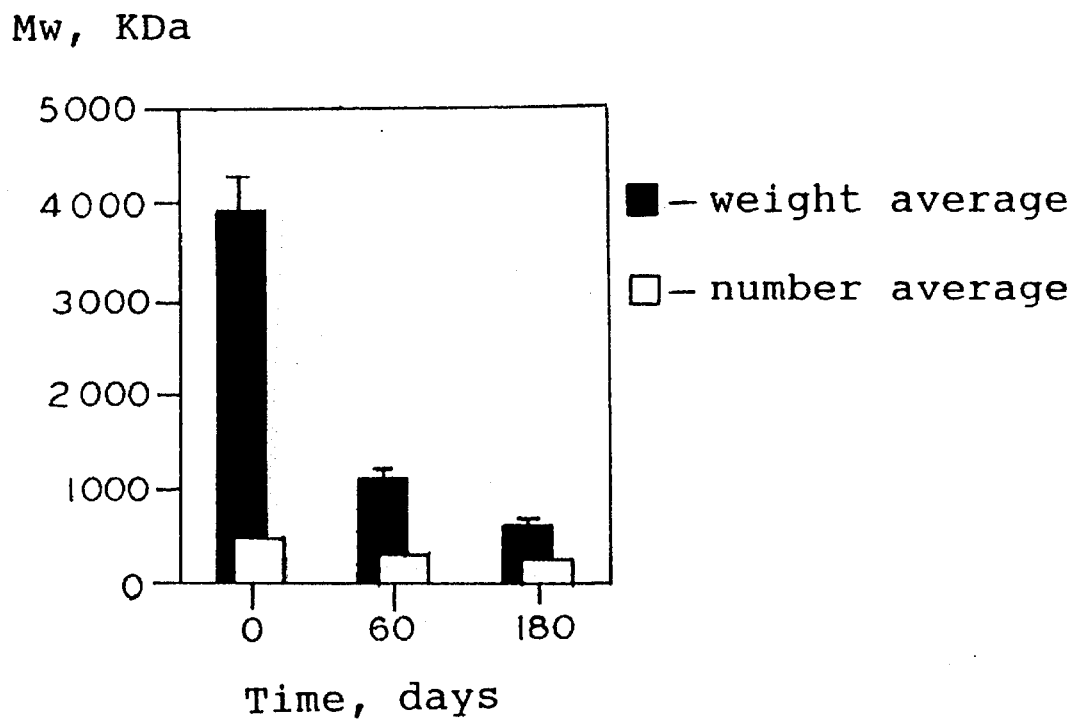
Figure 3B:
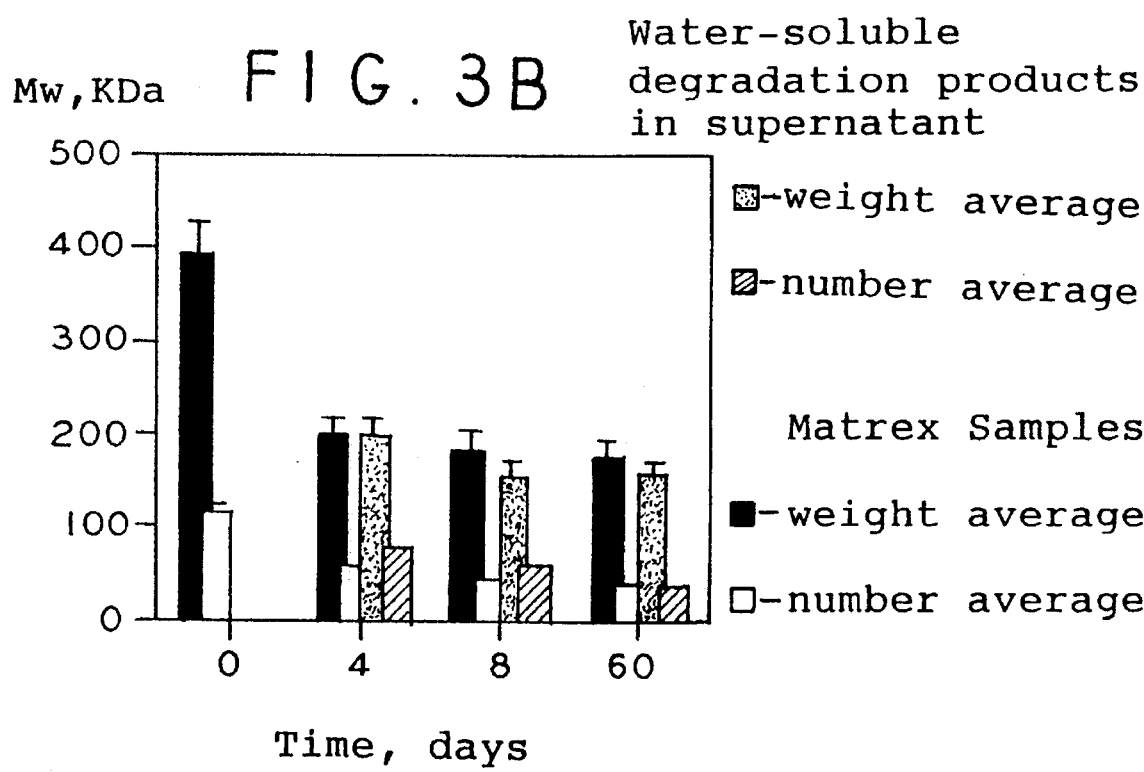

The second mechanism by which the antigens can be released from microspheres is through the erosion of the polymer matrix making up the microsphere. Erosion can occur through the reversal of the gelation reaction, resulting in the solubilization of polymer molecules and their return to the surrounding aqueous environment. Degradation of polyphosphazene microspheres was studied in saline solution (pH 7.4) by monitoring mass loss, molecular weights of polymer matrices and formation of soluble products. Erosion profiles for PCPP microspheres of varied molecular weights are shown in FIG. 2. No detectable mass loss was observed during 20 days incubation of high molecular weight PCPP microspheres in solution, and for the period of time extended to 180 days. However GPC data show significant decrease in polymer molecular weight during the same period of time (FIG. 3a). The mechanism of degradation apparently can involve intramolecular carboxylic group catalysis. Use of low molecular weight PCPP for microsphere preparation leads to significant erosion of the hydrogel during the first 10 days and a decrease in molecular weight of polymer (FIG. 3b). Water-soluble polymeric products of practically the same molecular weight as in the matrix were detected.

These data indicate that there is a molecular weight threshold of approximately 200 KDa in the release of polyphosphazene from the matrix into the solution in this system. However, polymer solubility also depends on the amount of calcium ions (or other multivalent cations or polymers) held by the matrix and the ionization degree of macromolecules. The observed differences in the erosion of PCPP are of prime importance for the design of antigen delivery systems.

Polyphosphazenes can be efficiently tailored by incorporating appropriate side-groups to provide a controllable set of properties, including hydrolytic degradability. Introduction of a hydrolysis-sensitive pendant group, such as glycinato group, increases the degradation rate in an aqueous environment. Cleavage of an external P-N bond occurring in neutral media in these aminophosphazenes to yield hydroxy derivatives confers hydrolytic instability in the polymer.

Figure 4:
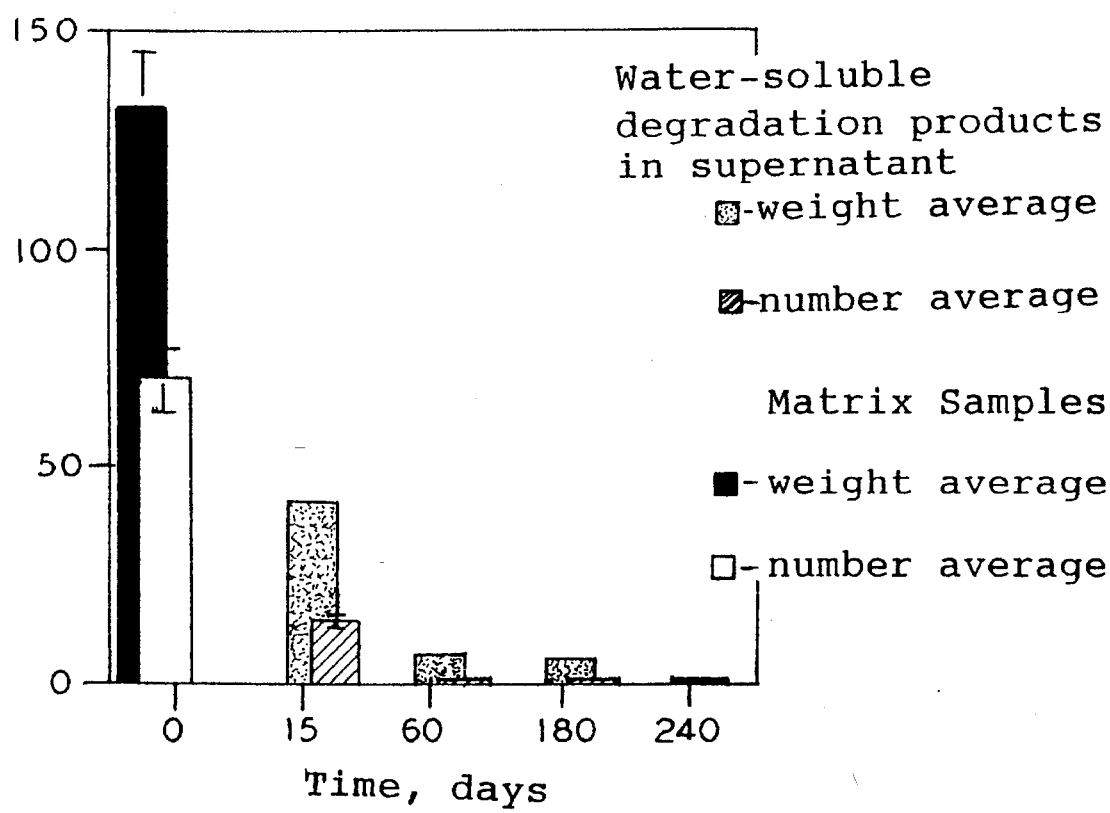

Poly[di(carboxylatophenoxy)phosphazene-co-di(glycinato) phosphazene] (PC-GlPP) containing 10% of glycinato groups was used for the preparation of microspheres and degradation studies. Erosion rates for these polymer hydrogels also depend on the molecular weight of polyphosphazenes. PC-GlPP with average molecular weight 130 KDa has a 100% mass loss within 3 days, as shown by FIG. 2. The GPC analysis of matrix and soluble products shows in FIG. 4 that a 240 day incubation in an aqueous environment results in breakdown of the polymer backbone leading to fragments with molecular weights lower than 1 KDa and inorganic phosphate. Coating hydrogel microspheres with Poly-L-lysine (M.W. 62 KDa) to yield a polyelectrolyte complex membrane significantly decreases the erosion rate by 2.5 times apparently because of steric hindrances, providing an additional approach to control the degradation and stability of polyphosphazene microspheres.

Effect of Crosslinking Agents

Figure 5:
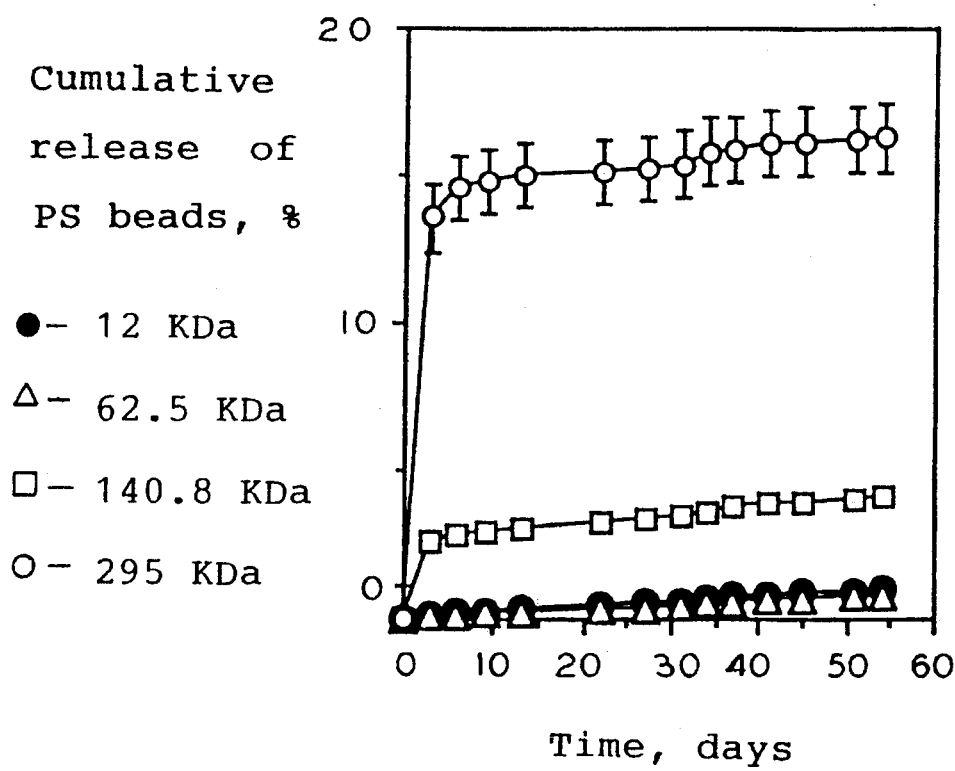

The third means by which one can regulate the release of antigen from microspheres is by coating the polyphosphazene microspheres with poly-L-lysine or a similar polyion to form a semi-permeable membrane on the outside of the microspheres. The microsphere core can then be liquified by the addition of chelating agents such as EDTA which reverse the gelation process and result in the solubilization of the polyphosphazene matrix. The degree of permeability can be regulated by the size of the polyion that is used in the coating process. The percent release from microspheres crosslinked with poly-L-lysines ranging in molecular weight from 12 to 295 KDa is shown in FIG. 5. As the molecular weight of the poly-L-lysine increases, the permeability of the coating increases, resulting in an increased release of 20 nm polystyrene beads from the microsphere.

The ability to vary the polyphosphazene concentration in the microspheres, alter the side chains on the polymer and coat microspheres with poly-L-lysine makes it possible to formulate microspheres that will release antigens with pulsatile and/or sustained release kinetics. The manipulability of this polymer system combined with the very gentle conditions for gelation and microsphere formation make this polymer system particularly desirable for developing single dose vaccines which may elicit both antibody and cellular immune responses.

EXAMPLE 3

Efficacy of Influenza vaccine encapsulated in alginate administered orally to mice as measured by In vitro and in vivo immune response studies Microencapsulated antigens were used to immunize mice by the oral route. The kinetics of the immune response were first determined by in vitro assays for humoral immunity. The use of in vivo studies allows determination of the capacity to effect antibody class switching, the effect of dose and route of immunization on the rapidity, amplitude and duration of the immune response, and the need for boosting the immune response. ELISA was used to evaluate total antigen specific responses as well as subclasses of IgG response, as described below. CTL assays could be performed to evaluate the cell mediated responses.

As described in detail below, tetanus toxoid (Connaught Laboratories) and influenza virus were encapsulated for the immunogenicity studies. Microencapsulated antigens were prepared and quantitated as described above. The antigen concentration in alginate and polyphosphazene microspheres as determined by SDS-PAGE was adjusted with sterile deionized water before administration.

Female 7 to 8 week old BALB/c mice were randomized into groups of five. Thirty micrograms of flu antigen were administered orally by intubation. Blood samples were taken from the retroorbital sinus of $CO_2$ anaesthetized mice. Mice were euthanized with $CO_2$ in an inhalation chamber.

The influenza mouse disease model system developed by Novak at al., Vaccine, 11:55–60 (1992), could be used to study the protection afforded by immunization with microencapsulated influenza. Mice are challenged at various times after immunization and the levels of virus replication in various organs determined. Although in previous studies parenteral immunization did not completely protect the nose and trachea, it does completely protect against virus propagation in the lungs. Thus, vaccine efficacy can be evaluated on the basis of the level of virus replication in the lungs.

Influenza was grown in eggs according to standard methods and quantitated by protein, hemagglutination and plaque assays. Influenza was formalin inactivated by the addition of a 38% formaldehyde solution at a final dilution of 1:4000. Virus infectivity was also inactivated by exposure to gamma irradiation from a $^{60}Co$ source to $1.2\times10^6$ rad.

Anti-influenza specific antibodies in mouse serum were determined by ELISA in 96-well microtiter plates coated with 10 µg/ml of influenza infected MDCK cell lysate in sodium carbonate buffer pH 9.6. Sites available for non-specific binding of protein after coating and washing were blocked by adding 2.5% BSA in PBS solution. After blocking and washing, two-fold serial dilutions of sera in 1% BSA/PBS were added to the wells. Unbound serum was washed away and horseradish peroxidase-labelled goat anti-mouse IgG added. Unbound conjugate was washed away and serum antibody detected by adding the substrate o-phenylenediamine dihydrochloride. The reaction was stopped by the addition of 2 M $H_2SO_4$ and the absorbance read at 490 nm. The endpoint titers are the reciprocal of the greatest sample dilution producing a signal significantly greater than that of an antibody negative sample at the same dilution.

The IgG isotypes of the ELISA reactive influenza specific antibodies were determined by the detection of murine antibodies bound to the antigens. Horseradish peroxidase labelled sheep anti-mouse antibody specific for mouse IgG subclasses 1, 2a, 2b and 3 was reacted with the mouse antibodies bound to the antigen in the ELISA plates.

The influenza hemagglutination inhibition antibody assay was done with heat-inactivated mouse serum that had been incubated for 30 minutes with 10% chicken red blood cells to remove non-specific inhibitors. Two fold dilutions of sera were added to a 96 well microtiter plate and 8 HA units of virus suspension in an equal volume were added to each well and incubated at room temperature for 30 minutes. A 0.5% suspension of chicken red blood cells was added to each well and incubated at room temperature for 45–60 minutes. The HI titers are expressed as the reciprocal of the highest dilution that completely inhibits hemagglutination of erythrocytes.

In the first group of studies, five groups of BALB/c mice, consisting of two mice per group, were immunized by oral intubation with sterile deionized water (Group I), empty alginate microspheres (Group II), alginate microspheres containing 30 µg Influenza (Group III), alginate microspheres containing 30 µg Influenza plus 10 µg cholera toxin (CT) admixed (Group IV), or 30 µg soluble Influenza (Group V). Blood and fecal samples were collected on days 7, 14, 21 and 28 post-immunization and the class specificity of influenza antibody reactivity was determined.

Animals were immunized as described above with influenza antigen encapsulated in alginate, alone or in combination with cholera toxin.

Figure 6A:
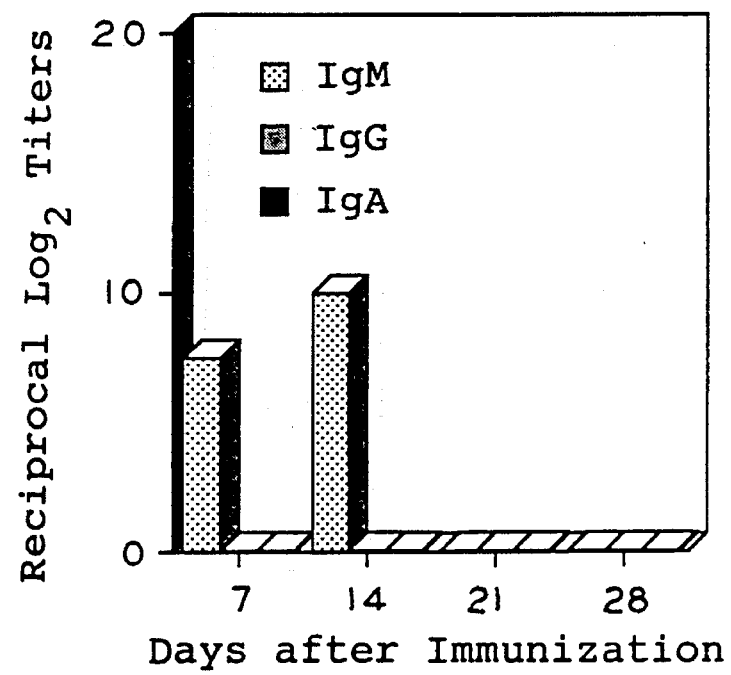
Figure 6B:
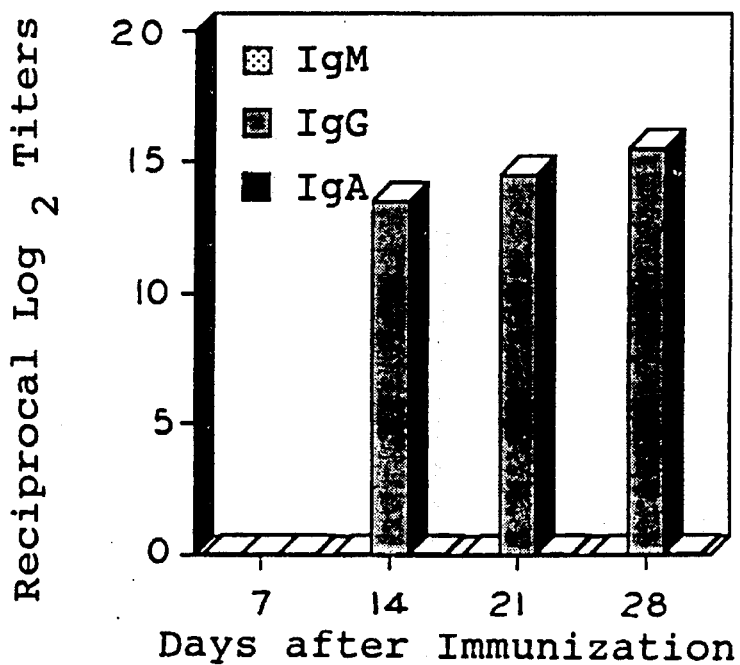
Figure 6C:
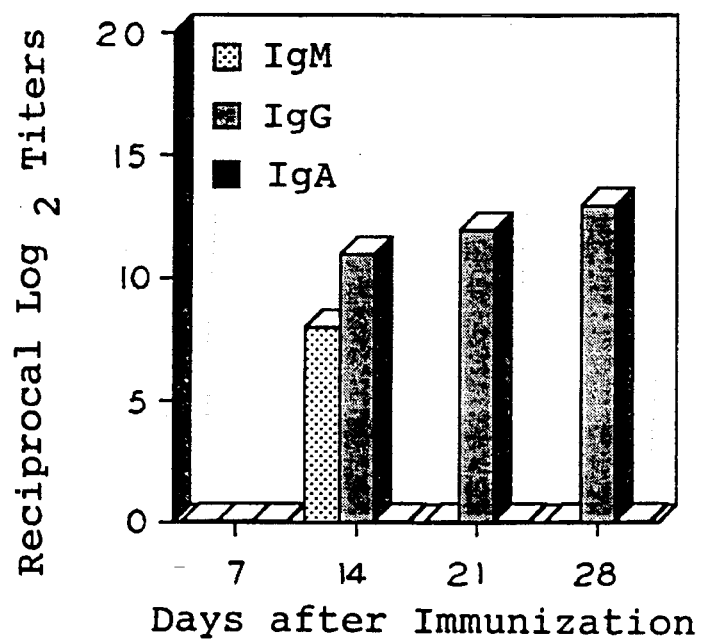

The results with alginate encapsulated influenza antigen are shown in FIGS. 6a, 6b, and 6c. Control mice that received no influenza antigen (groups I and II) showed no flu-specific serum IgM or IgG responses. Soluble influenza (Group V) induced a low IgM titer at day 7 that persisted at least through day 14 but there was no detectable IgG response, as shown in FIG. 6a. Encapsulated flu together with CT induced high levels of flu-specific IgG at day 14 post-immunization, as shown in FIG. 6b. These levels were maintained up to day 28. Alginate encapsulated flu alone induced flu-specific IgG titers that were equivalent to those seen in the animals that received the microsphere influenza-CT admixture, as shown in FIG. 6c. Good antibody titers were observed as early as 14 days, with high titers of IgG present through at least 77 days.

Figure 7:
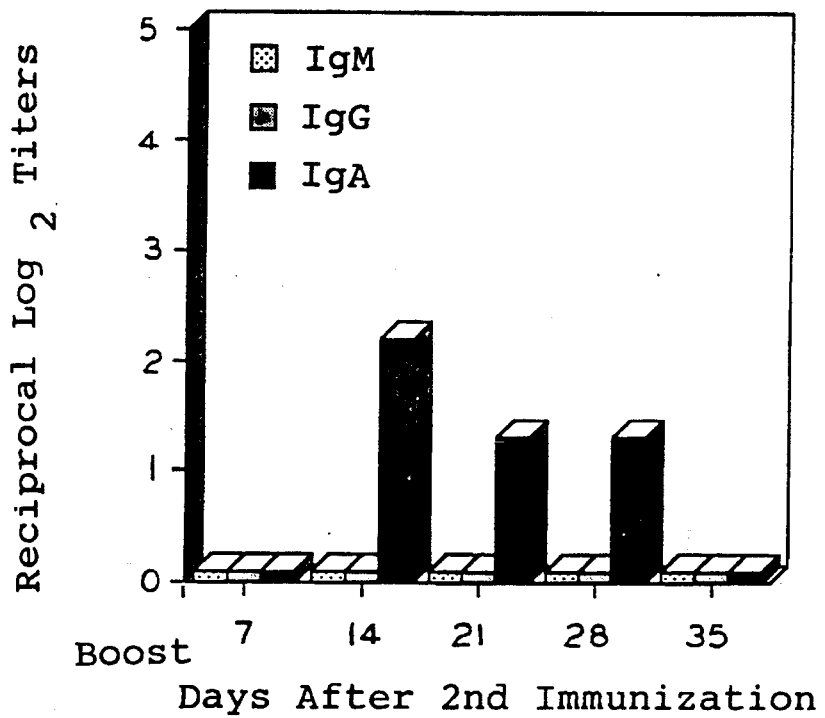

Animals immunized with alginate encapsulated influenza plus cholera toxin were boosted at 35 days post primary immunization. The results are shown in FIG. 7. Boosting with influenza in combination with cholera toxin elicits production of IgA, as measured in the fecal samples.

In summary, the alginate encapsulated flu did not require the mucosal adjuvant CT for the induction of antigen specific IgM and IgG in the sera. The results obtained with alginate encapsulated influenza show that a single oral dose in the absence of CT elicits high flu specific serum IgG responses. Results in FIG. 7 show that IgA antibodies are induced following a single oral boost with influenza encapsulated in alginate with CT.

EXAMPLE 4

Production of Antibody by oral administration of Influenza vaccine encapsulated in polyphosphazene to mice as measured by In vitro and in vivo immune response studies The same protocol was followed for immunization of animals with influenza alone or in combination with cholera toxin, encapsulated in polyphosphazene microspheres, as described above.

Figure 8:
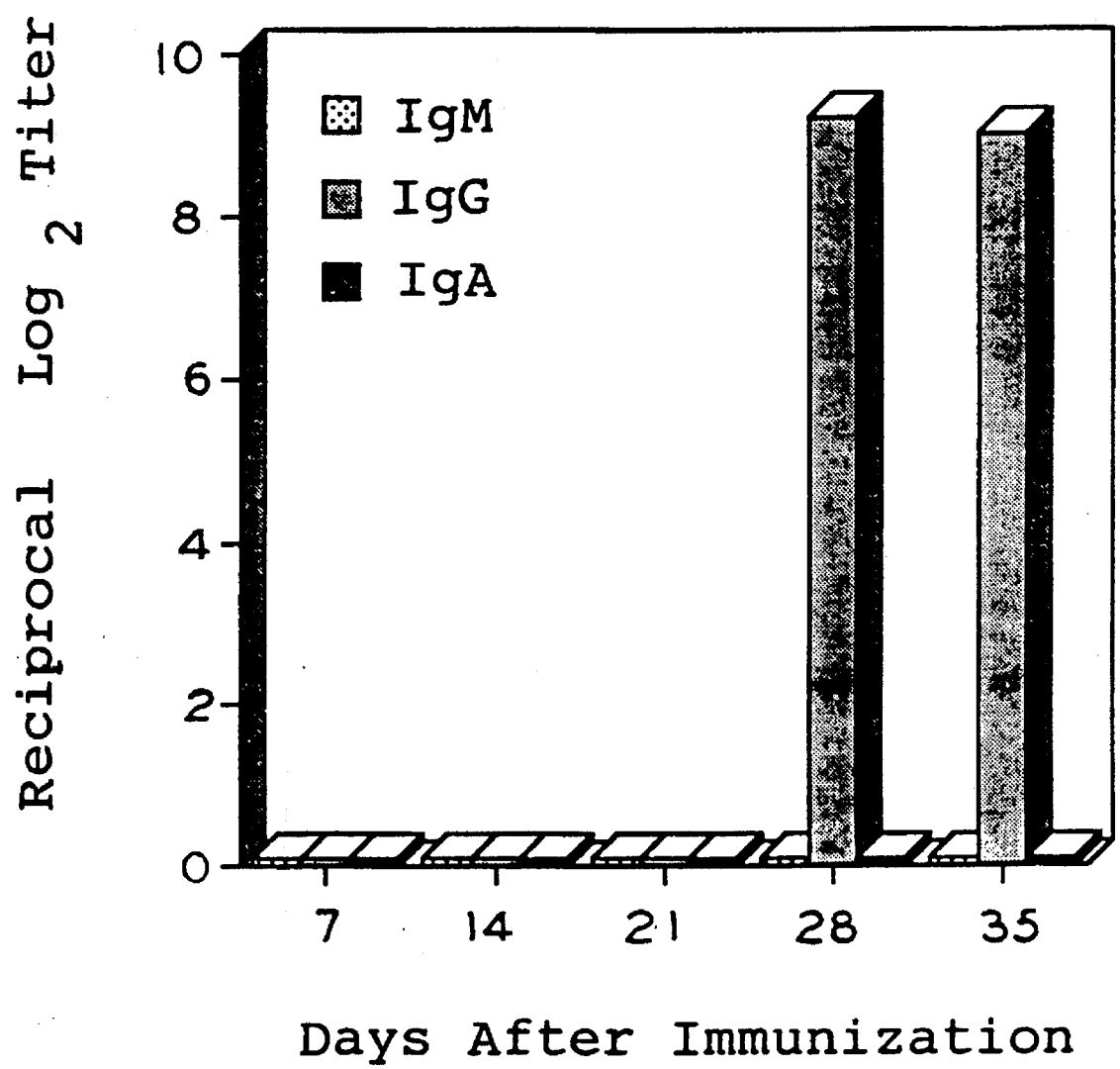

The results are shown in FIG. 8. In the absence of cholera toxin there is no production of anti-influenza antibodies measurable in either the serum or the feces. With the combination of influenza antigen and cholera toxin there is production of IgG in a similar manner to that demonstrated with alginate encapsulated antigen (FIG. 6b), although slightly delayed in onset.

EXAMPLE 5

Intranasal immunization of mice with microencapsulated tetanus toxoid

Mice were divided into four groups and inoculated intranasally with (1) tetanus toxoid in water (9 animals); (2) tetanus toxoid in alginate microspheres (9 animals); (3) tetanus toxoid in PCPP microspheres (10 animals); and (4) tetanus toxoid in microspheres consisting of 95% alginate/ 5% PCPP (9 animals). In each case 50 µg of antigen was administered. Mice were assayed by ELISA for antibody production after two weeks (serum) and three weeks (bronchial and nasal washes). The results are shown in Table 1.

These results clearly demonstrate that intranasal administration of antigen in a polyphosphazene or alginate/polyphosphazene microsphere induces a serum IgG response. Moreover, the results demonstrate that this method of administration can be used to elicit production of IgA molecules, when the antigen is encapsulated within the combination of alginate and PCPP.

TABLE 1

Intranasal inoculation with microencapsulated tetanus toxoid.

| Group/Animal | treatment | anti-tetanus toxoid titer (log2) | |
|---|---|---|---|
| | | IgG | IgA |
| 1 | tetanus toxoid | <256(<8) | |
| 2 | tetanus toxoid | <256(<8) | |
| 3 | tetanus toxoid | <256(<8) | |
| 4 | tetanus toxoid | <256(<8) | |
| 5 | tetanus toxoid | <256(<8) | |
| 6 | tetanus toxoid | 256(8) | |
| 7 | tetanus toxoid | 256(8) | |
| 8 | tetanus toxoid | <256(<8) | |
| 9 | tetanus toxoid | <256(<8) | |
| 10 | tetanus toxoid in alginate microspheres | <256(<8) | |
| 11 | tetanus toxoid in alginate microspheres | <256(<8) | |
| 12 | tetanus toxoid in alginate microspheres | <256(<8) | |
| 13 | tetanus toxoid in alginate microspheres | <256(<8) | |
| 14 | tetanus toxoid in alginate microspheres | <256(<8) | |
| 15 | tetanus toxoid in alginate microspheres | <256(<8) | |
| 16 | tetanus toxoid in alginate microspheres | <256(<8) | |
| 17 | tetanus toxoid in alginate microspheres | <256(<8) | |
| 18 | tetanus toxoid in alginate microspheres | <256(<8) | |
| 19 | tetanus toxoid in PCPP microspheres | 512(9) | <2(<1) |
| 20 | tetanus toxoid in PCPP microspheres | 2048(11) | <2(<1) |
| 21 | tetanus toxoid in PCPP microspheres | 512(9) | <2(<1) |
| 22 | tetanus toxoid in PCPP microspheres | 512(9) | |
| 23 | tetanus toxoid in PCPP microspheres | 2048(11) | |
| 24 | tetanus toxoid in PCPP microspheres | 512(9) | |
| 25 | tetanus toxoid in PCPP microspheres | 1024(10) | |
| 26 | tetanus toxoid in PCPP microspheres | 1024(10) | |
| 27 | tetanus toxoid in PCPP microspheres | 1024(10) | |
| 28 | tetanus toxoid in PCPP microspheres | 512(9) | |
| 29 | tetanus toxoid in Alginate/5% PCPP ms | 4096(12) | 8(3) |
| 30 | tetanus toxoid in Alginate/5% PCPP ms | 4096(12) | 32(5) |
| 31 | tetanus toxoid in Alginate/5% PCPP ms | 512(9) | 8(3) |
| 32 | tetanus toxoid in Alginate/5% PCPP ms | 256(<8) | |
| 33 | tetanus toxoid in Alginate/5% PCPP ms | 2048(11) | |
| 34 | tetanus toxoid in Alginate/5% PCPP ms | 2048(11) | |
| 35 | tetanus toxoid in Alginate/5% PCPP ms | 2048(11) | |
| 36 | tetanus toxoid in Alginate/5% PCPP ms | 2048(11) | |
| 37 | tetanus toxoid in Alginate/5% PCPP ms | 1024(10) | |

EXAMPLE 6

Parenteral immunization of mice with tetanus toxoid encapsulated in microspheres and comparison with immunization with conventional adjuvants Traditionally, most injected non-replicating vaccines have required multiple doses to achieve sufficient serum antibody titers to be protective. For obvious reasons, it would be much more desirable to achieve protection with a single inoculation. Therefore, the effect of polyphosphazene on the immunogenicity of antigens was examined in mice that were immunized subcutaneously with a single dose. Antigen formulated in water, alum and complete Freund's adjuvant was included in many experiments as a comparator.

The immunogenicity of tetanus toxoid antigen formulated in polymeric microspheres composed of alginate or polyphosphazene was compared to soluble tetanus toxoid and tetanus toxoid in the standard adjuvants, alum and complete Freund's adjuvant (CFA). Groups of five mice were immunized by the subcutaneous route with 20 μg of tetanus toxoid.

The results are shown in Table 2. The anti-tetanus toxoid serum immune responses were assayed by ELISA. Soluble tetanus toxoid antigen and alginate microencapsulated tetanus toxoid induced a maximum titer of 512 by week 13. Polyphosphazene microspheres containing tetanus toxoid induced higher antibody titers at earlier times post immunization than alum or complete Freund's adjuvanted tetanus toxoid. Furthermore, polyphosphazene microspheres containing tetanus toxoid induced antibody titers that were still rising at 13 weeks post immunization. At this late time point, tetanus toxoid in polyphosphazene microspheres had elicited a titer of 65,536, which was approximately 100 times as strong a response as seen for soluble tetanus toxoid and as good as or slightly better (two to four fold higher) than was seen for alum and complete Freund's adjuvant. Polyphosphazene microspheres were clearly superior to alginate microspheres in the induction of antibodies to tetanus toxoid.

TABLE 2

ELISA Titers in Mice Inoculated SC with Tetanus Toxoid

| | anti TT ELISA titer | | | | |
|---|---|---|---|---|---|
| | week 3 | week 5 | week 7 | week 9 | week 13 |
| TT in Water | <256 | 256 | 256 | 256 | 512 |
| TT in Alginate MS | 256 | 512 | 512 | 512 | 512 |
| TT in Alum | 2048 | 8192 | 16384 | 32768 | 32768 |
| TT in CFA | 2048 | 16384 | 16384 | 32768 | 16384 |
| TT in Poly- | 8192 | 16384 | 32768 | 32768 | 65536 |

TABLE 2-continued

ELISA Titers in Mice Inoculated SC with Tetanus Toxoid

| | anti TT ELISA titer | | | | |
|---|---|---|---|---|---|
| | week 3 | week 5 | week 7 | week 9 | week 13 |
| phosphazene MS | | | | | |

The dose dependent effect of immunization with tetanus toxoid was examined by immunizing mice with varying amounts of tetanus toxoid formulated into polyphosphazene microspheres or complete Freund's adjuvant.

The results are shown in Table 3. The immunogenicity of tetanus toxoid in polyphosphazene microspheres compared very favorably with complete Freund's adjuvant formulated tetanus toxoid. At all time points and tetanus toxoid doses, the ELISA titers for the two formulations were within a two-fold dilution of each other.

TABLE 3

ELISA Titers in Mice Inoculated SC with Tetanus Toxoid anti-TT ELISA titer

| | TT + polyphosphazene | | | | TT + complete Frends adjuvant | | | |
|---|---|---|---|---|---|---|---|---|
| TT (µg) | week3 | week5 | week7 | week9 | week3 | week5 | week7 | week9 |
| 25 | 32768 | 65536 | 131072 | 131072 | 16384 | 131072 | 262144 | 262144 |
| 5 | 8192 | 32768 | 65536 | 65536 | | | | |
| 2.5 | | | | | 4096 | 16384 | 32768 | 16384 |
| 1 | 4096 | 16384 | 65536 | 65536 | 16384 | 32768 | 32768 | 32768 |
| 0.2 | 2048 | 4096 | 8192 | 8192 | 1024 | 4096 | 4096 | 4096 |
| 0.04 | <256 | <256 | 256 | 256 | <256 | <256 | <256 | <256 |

EXAMPLE 7

Parenteral Immunization of mice with influenza particles formulated in polymeric microspheres or with adjuvant Mice were also immunized with 5 µg of formalin inactivated influenza virus particles formulated in polymeric microspheres, alum and complete Freund's adjuvant to determine if the relative efficiencies of the formulations would be the same for an enveloped virus as they were for tetanus toxoid.

The results are shown in Table 4. Again, polyphosphazene microspheres were as efficient as complete Freund's adjuvant but much more efficient than water, alum or alginate microspheres at inducing a very high titer anti-flu immune response. In contrast to the tetanus toxoid results, alum adjuvanted influenza was no better than soluble influenza and alginate microencapsulated influenza in eliciting a rather low titer anti-flu response. Taken together, these results demonstrate that polyphosphazene microspheres containing an antigen provoke an antibody response equal in magnitude to complete Freund's adjuvant formulated antigens.

TABLE 4

ELISA Titers in Mice Inoculated SC with x-31 Influenza

| | anti- flu ELISA titer | | | | |
|---|---|---|---|---|---|
| | week 3 | week 5 | week 7 | week 9 | week 13 |
| Flu in Water | 256 | 1024 | 1024 | 512 | 512 |
| Flu in Alginate MS | 512 | 1024 | 2048 | 2048 | 2048 |
| Flu in Alum | <256 | 512 | 1024 | 2048 | 2048 |
| Flu in CFA | 8192 | 16384 | 32768 | 32768 | 16384 |
| Flu in Polyphosphazene MS | 8192 | 32768 | 32768 | 8192 | 16384 |

The mouse sera were tested for the presence of functional antibodies by hemagglutination inhibition and neutralization assays. The results of the hemagglutination assay are shown in Table 5. As measured by the HAI assay, the polyphosphazene microspheres containing flu elicited an antibody titer of 1280 by week 7, while the Freund's adjuvanted flu, as well as the flu in alum and alginate microspheres, elicited either no detectable or very low HAI titers.

TABLE 5

Hemagglutination Inhibition Assay titers in mice inoculated SC with x-31 Influenza

| | HAI titer | | | | |
|---|---|---|---|---|---|
| | week 3 | week 5 | week 7 | week 9 | week 13 |
| Flu in Water | neg | neg | neg | 40 | neg |
| Flu in Alginate MS | neg | neg | 40 | 40 | 40 |
| Flu in Alum | neg | neg | neg | neg | neg |
| Flu in CFA | neg | neg | neg | 40 | neg |
| Flu in Polyphosphazene MS | 320 | 640 | 1280 | 1280 | 1280 |
| Water* | neg | neg | neg | neg | neg |

*Negative control had a titer of 20 due to non-specific serum hemagglutination inhibitors. Neg ≦ 20.

Antibodies that neutralize influenza infectivity were assayed in a 50% plaque reduction assay. Flu in polyphosphazene microspheres induced a detectable titer of 800 by week 13, whereas, flu in water and complete Freund's adjuvant did not elicit detectable neutralizing antibody titers. The HAI and neutralization assays are sensitive functional antibody assays for influenza. Thus, the immune response engendered by polyphosphazene microspheres is superior to complete Freund's adjuvant.

TABLE 6

Influenza Plaque Reduction Assay

|  | week 13 |
| --- | --- |
| Flu in Polyphosphazene MS | 800 |
| Flu in Water | <200 |
| Flu in CFA | <200 |
| Normal mouse serum | <200 |

The IgG isotypes of the antibodies induced by these formulations were determined by an ELISA assay. The results are shown in Table 7. Alum adjuvanted influenza elicited a purely IgG1 response as expected. Flu formulated in Complete Freund's Adjuvant induced mostly an IgG1 response that peaked by week 7 and was waning by week 13. Flu formulated in alginate and polyphosphazene microspheres also induced largely an IgG1 response that by week 7 was higher than flu formulated in alum. Again, polyphosphazene microsphere formulated antigen induced titers that compared very favorably with those induced by complete Freund's adjuvant formulated antigen. Polyphosphazene microspheres like complete Freund's adjuvant was able to induce significant levels of IgG2a and IgG2b antibodies. A significant difference in the immune response was found in the level of activity detected in the IgG3 isotype. Polyphosphazene microspheres were the only formulation able to induce a significant IgG3 antibody titer.

TABLE 8

Flu ELISA Isotyping Results

| | 3 Weeks | | | | 7 Weeks | | | | 13 Weeks | | | |
| --- | --- | --- | --- | --- | --- | --- | --- | --- | --- | --- | --- | --- |
| | IgG1 | IgG2A | IgG2B | IgG3 | IgG1 | IgG2A | IgG2B | IgG3 | IgG1 | IgG2A | IgG2B | IgG3 |
| Flu in alginate MS | 1024 | <256 | 256 | <256 | 65536 | 1024 | 512 | <256 | 8192 | 512 | <256 | <256 |
| Flu in PPP MS | 8192 | 4096 | 512 | 512 | 131072 | 16384 | 1024 | 4096 | 16384 | 16384 | 2048 | 1024 |
| Flu in Alum | 512 | <256 | <256 | <256 | 16384 | <256 | <256 | <256 | 8192 | <256 | <256 | <256 |
| Flu in CFA | 8192 | 1024 | 4096 | <256 | >52428 | 8192 | 4096 | <256 | 32768 | 2048 | 2048 | <256 |
| Flu in Water | 256 | 512 | 256 | <256 | 2048 | 1024 | 256 | <256 | 1024 | 512 | <256 | <256 |

Modifications and variations of the present invention, polymer adjuvants and methods of synthesis and use in vaccine compositions, will be obvious to those skilled in the art from the foregoing detailed description. Such modifications and variations are intended to come within the scope of the appended claims.

We claim:

1. A method of treating an animal to elicit an immune response comprising: treating an animal to elicit an immune response by mucosally administering to the animal a vaccine composition comprising hydrogel microparticles, wherein said microparticles comprise a polyphosphazene polymer and said microparticles contain an effective amount of an antigen to elicit an immune response, wherein the microparticles are 200 microns or less in diameter.

2. The method of claim 1 wherein the microspheres are administered to mucosal surfaces.

3. The method of claim 2 wherein the route to the mucosal surfaces is intratracheal.

4. The method of claim 2 wherein the route to the mucosal surfaces is intranasal.

5. The method of claim 2 wherein the mucosal surfaces is selected from the group consisting of rectal and vaginal.

6. The method of claim 2 wherein the route to the mucosal surfaces is orally.

7. The method of claim 1 wherein the microparticles have a diameter of between one micron and fifteen microns.

8. The method of claim 1 wherein the antigen is selected from the group consisting of compounds derived from cells, bacteria, and virus particles, wherein the compound is selected from the group consisting of proteins, peptides, polysaccharides, glycoproteins, glycolipids, and nucleic acids.

9. The method of claim 8 wherein the antigen is derived from an organism selected from the group consisting of rotavirus, measles, mumps, rubella, polio, hepatitis A and B, herpes viruses, *Haemophilus influenza*, *Clostridium tetani*, influenza, *Corynebacterius diphtheria*, and *Neisseria gonorrhea*.

10. The method of claim 1 wherein the polymer is covalently conjugated with the antigen.

11. The method of claim 1 wherein the microparticles are administered in combination with a material protecting the microparticles from the acid pH of the stomach.

12. The method of claim 1 wherein the microparticles have different release rates.

13. The method of claim 1 wherein the polyphosphazene polymer is a crosslinked polyphosphazene.

14. The method of claim 13 wherein the polymer is ionically crosslinked.

15. The method of claim 1 wherein the polyphosphazene is biodegradable.

16. The method of claim 1 wherein the microparticles comprise polyphosphazene and alginate.

17. The method of claim 1 wherein the polyphosphazene contains carboxylatophenoxy pendant groups.

18. The method of claim 1 wherein the polyphosphazene is a copolymer which comprises poly [di(carboxylatophenoxy)] phosphazene.

19. The process of claim 1 wherein the polyphosphazene polymer is poly [di (carboxylatophenoxy) phosphazene-co-di (chloro) phosphazene-co-(carboxylatophenoxy) (chloro)phosphazene].

20. The method of claim 1 wherein the polyphosphazene is poly[dicarboxylatophenoxy phosphazene].

* * * * *